United States Patent

Liaw et al.

[11] Patent Number: 6,136,571
[45] Date of Patent: Oct. 24, 2000

[54] METHOD OF PRODUCING SACCHARIDE PREPARATIONS

[75] Inventors: Gin C. Liaw, Decatur, Ill.; Sven Pedersen, Gentofte, Denmark; Hanne Vang Hendriksen, Holte, Denmark; Allan Svendsen, Birkerød, Denmark; Bjarne Rønfeldt Nielsen, Virum, Denmark; Ruby Illum Nielsen, Farum, Denmark

[73] Assignee: Novo Nordisk A/S, Bagsvaerd, Denmark

[21] Appl. No.: 09/499,531

[22] Filed: Feb. 10, 2000

Related U.S. Application Data

[63] Continuation of application No. 09/198,672, Nov. 23, 1998, which is a continuation-in-part of application No. 09/107,657, Jun. 30, 1998, abandoned, which is a continuation-in-part of application No. 08/979,673, Nov. 26, 1997, abandoned.

[51] Int. Cl.[7] ............ C12P 19/14; C12P 19/20; C12P 19/22; C13K 13/00; C13D 3/16
[52] U.S. Cl. ............ 435/96; 435/98; 435/99; 127/40; 127/55
[58] Field of Search ............ 127/40, 55; 435/96, 435/98, 99

[56] References Cited

U.S. PATENT DOCUMENTS 3,720,583  3/1973  Fischer ............ 195/31
4,594,322  6/1986  Thomson et al. ............ 435/95

FOREIGN PATENT DOCUMENTS 0452238    10/1991   European Pat. Off. ............ C13K 1/00
0 481 903 A1  4/1992   European Pat. Off. .
WO 98/03639   1/1998   WIPO .

OTHER PUBLICATIONS

Mitsuo Tanaka et al., "Removal of Lignin and Reuse of Cellulases for Continuous Saccharification of Lignocelluloses", Biotechnology and Bioengineering, vol. 32, (1988) No Month Provided pp. 897–902.

*Primary Examiner*—David Brunsman
*Attorney, Agent, or Firm*—Steve T. Zelson, Esq.; Elias J. Lambiris, Esq.

[57] ABSTRACT

The present invention relates to a method for the production of saccharide preparations, i.e., syrups, by saccharifying a liquefied starch solution, which method comprises a saccharification step during which step one or more enzymatic saccharification stages takes place, and the subsequent steps of one or more high temperature membrane separation steps, and re-circulation of the saccharification enzyme, in which method the membrane separation steps are carried out as an integral part of the saccharification step. In another specific aspect, the invention provides a method of producing a saccharide preparation, which method comprises an enzymatic saccharification step, and the subsequent steps of one or more high temperature membrane separation steps and re-circulation of the saccharification enzyme.

15 Claims, 5 Drawing Sheets

SACC. = Saccharification
U.F. = Ultra filtration

SACC. = Saccharification
M.F. = Micro filtration
U.F. = Ultra filtration
N.F. = Nano filtration

METHOD OF PRODUCING SACCHARIDE PREPARATIONS

CROSS-REFERENCE TO RELATED APPLICATIONS

This application is a continuation of U.S. Ser. No. 09/198,672 filed on Nov. 23, 1998, which is a continuation-in-part of U.S. Ser. No. 09/107,657 filed on Jun. 30, 1998, now abandoned, which is a continuation-in-part of U.S. Ser. No. 08/979,673 filed on Nov. 26, 1997, now abandoned, the contents of which are fully incorporated herein by reference.

The present invention relates to the production of mono and/or oligosaccharides from starch, including dextrose, trehalose, isomaltooligosaccaharides, cyclodextrins and maltooligosaccharides. In a specific aspect, the invention provides a method of saccharifying a liquefied starch solution, which method comprises a saccharification step during which step one or more enzymatic saccharification stages takes place, and the subsequent steps of one or more high temperature membrane separation steps, and re-circulation of the saccharification enzyme, in which method the membrane separation steps are carried out as an integral part of the saccharification step.

In another specific aspect, the invention provides a method of producing a mono and/or oligosaccharide, such as dextrose, trehalose, isomaltooligosaccaharide, cyclodextrins and maltooligosaccharide preparation, which method comprises an enzymatic saccharification step, and the subsequent steps of one or more high temperature membrane separation steps and re-circulation of the saccharification enzyme.

BACKGROUND ART

Saccharides may be grouped into the following two groups: 1) monosaccharides and 2) saccharides which can be hydrolyzed into monosaccharides. Such saccharides which can be hydrolyzed into from 2–10 monosaccharides are termed "oligosaccharides", whereas such saccharides which can be hydrolyzed into more than 10 monosaccharides are termed "polysaccharides".

Starch to Sugar Conversion

In the case of converting starch into a sugar (e.g., the starch is depolymerized. A such depolymerization process consists of a pretreatment step and two or three consecutive process steps, viz. a liquefaction process, a saccharification process and dependent on the desired end product optionally an isomerization process.

Pre-treatment of Native Starch

Native starch consists of microscopic granules which are insoluble in water at room temperature. When an aqueous starch slurry is heated, the granules swell and eventually burst, dispersing the starch molecules into the solution. During this "gelatinization" process there is a dramatic increase in viscosity. As the solids level is 30–40% in a typically industrial process, the starch has to be thinned or "liquefied" so that it can be handled. This reduction in viscosity is today mostly obtained by enzymatic degradation.

Liquefaction

During the liquefaction step, the long chained starch is degraded into branched and linear shorter units (maltodextrins) by an α-amylase (e.g., Termamyl™). The liquefaction process is carried out at 105–110° C. for 5 to 10 minutes followed by 1–2 hours at 95° C. The pH lies between 5.5 and 6.2. In order to ensure an optimal enzyme stability under these conditions, 1 mM of calcium is added (40 ppm free calcium ions). After this treatment the liquefied starch will have a "dextrose equivalent" (DE) of 10–15.

Saccharification

After the liquefaction process the maltodextrins are converted into dextrose by addition of a glucoamylase (e.g., AMG™, available from Novo Nordisk) and a debranching enzyme, such as an isoamylase (e.g., U.S. Pat. No. 4,335,208) or a pullulanase (e.g., Promozyme™—see U.S. Pat. No. 4,560,651). Before this step the pH is reduced to a value below 4.5, maintaining the high temperature (above 95° C.) to inactivate the liquefying α-amylase to reduce the formation of short oligosaccharide called "panose precursors" which cannot be hydrolyzed properly by the debranching enzyme. The temperature is traditionally lowered to about 60° C., and glucoamylase and debranching enzyme are added. The saccharification process proceeds for 24–72 hours.

Normally, when denaturing the α-amylase after the liquefaction step about 0.2–0.5% of the saccharification product is the branched trisaccharide $6^2$-α-glucosyl maltose (panose) which cannot be degraded by a pullulanase. If active amylase from the liquefaction step is present during saccharification (i.e., no denaturing), this level can be as high as 1–2%, which is highly undesirable as it lowers the saccharification yield significantly.

The above pre-treatment and liquefaction steps may suitably be used for providing the liquefied starch for saccharification or hydrolyzing step.

Dextrose Syrups

Dextrose (D-glucose) syrups may be produced by enzymatic conversion of starch into sugars (e.g., as described above). Enzymatic conversion of starch into sugars involves the subsequent steps of liquefaction and saccharification. In this way a high dextrose syrup, usually of 95–96% DX (DX meaning percentage by weight of dextrose (D-glucose) calculated on the basis of dry substance (DS) of syrup) can be obtained. By-products are, e.g., maltose, isomaltose and panose. If syrups of a higher dextrose content is desired, purification may be accomplished by crystallization.

Maltooligosaccharide Syrups

Maltooligosaccharide syrups are syrups comprising from 40 to above 80% maltose (O-α-D-glucopyranosyl-(1-4)-D-glucopyranose). Maltose is a reducing water soluble disaccharide consisting of two glucose units linked in α-1,4 position.

Maltooligosaccharide syrups are today usually produced enzymatically as will be described further below.

Isomaltooligosaccharide Syrups

Isomaltooligosaccharide syrups are sometimes referred to as "Alo mixtures" and defines a mixture containing isomaltose (O-α-D-glucopyranosyl-(1-6)-D-glucopyranose), panose, isomaltotriose and several other branched oligosaccharides composed of four and five glucose residues. "Alo mixture" syrups may be produced enzymatically from starch using a thermostable bacterial α-amylase in the liquefaction step. In the following step the liquefied starch is hydrolyzed or saccharified using a β-amylase and a transglucosidase simultaneously.

Trehalose Syrups

Trehalose (α-D-glucopyranosyl α-D-glucopyranoside) is a non reducing disaccharide with two glucose residues bound by a α-1,1 linkage.

Enzymatic processes for producing trehalose from starch or maltooligosaccharides are described by, e.g., Kato et al., (1996), Biosci. Biotech. Biochem., 60 (3), p. 546–550); Kazuhisa et al. (1997), Starch 49, no. 1. p. 26–30; and in EP 764,720.

Cyclodextrin Syrups

Cyclodextrins are oligosaccharides with a closed-ring structure in which the glucose units are joined together by α-1,4 linkages. Cyclodextrins containing 6,7 or 8 glucose units are most common and are known as α, β and γ-CD, respectively.

Cyclodextrins may be produced enzymatically from starch using the enzyme Cyclodextrin glucanotransferase (E.C. 2.4.1.19), in short termed CGTase. CGTases catalyse the conversion of starch and similar substrates into cyclodextrins via an intramolecular transglycosylation reaction, thereby forming cyclodextrins of various sizes.

JP 3-224493 describes an enzymatic conversion of starch into sugars, in which process the saccharified solution is subjected to membrane fractionation to obtain a starch sugar fraction and a fraction containing high molecular dextrins, and feeding back the dextrin fractions to appropriate upstream points.

JP 1-191693 describes a saccharification process by which glucoamylase enzyme is added to liquefied starch at 50–60° C. to cause reaction, followed by continuous separation and recovery of the resulting glucose through a membrane.

JP 62-272987 describes a saccharification process by which glucoamylase enzyme is added to liquefied starch and the saccharification process is practiced inside a semipermeable membrane, and the glucose formed is discharged to the outside. The molecular weight distribution of the liquefied starch determines the addition of enzyme and the retention time.

Membrane Separation

Membrane separation processes includes the following four basic processes: reverse osmosis, nanofiltration, ultrafiltration and microfiltration.

Reverse osmosis is the tightest possible membrane process in liquid/liquid separation. Water is in principle the only material passing the membrane. Essentially all dissolved and suspended material is rejected. The more open types of reverse osmosis membranes are sometimes confused with nanofiltration.

Nanofiltration is similar to reverse osmosis, but the membrane is slightly more open. Monovalent ions can pass fairly freely through a nanofiltration membrane together with water. Polyvalent negative ions are rejected almost completely by a good nanofiltration membrane. It is to be understood that according to the present invention "nanofiltration" means filtration of dextrose containing permeate through a nanofiltration membrane having a pore size which allows passage of dextrose molecules while rejecting di- and trisaccharide molecules of glucose.

Ultrafiltration is a process where only the high molecular weight compounds, e.g., protein, and suspended solids are rejected. All low molecular weight compounds can pass the membrane freely. There is consequently no rejection of mono and disaccharides, salts, amino acids, organic acids, inorganic acids or sodium hydroxide.

Microfiltration is a process where ideally only suspended, visible solids are rejected, while even proteins pass the membrane freely.

Whereas aqueous mixtures containing dextrose, maltose and salts may be concentrated by diffusion through reverse osmosis or nanofiltration membranes, such membranes are normally not capable of purifying dextrose by removing the maltose and salts. Also, while conventional ultrafiltration provide means for purifying or separating compounds of different molecular weight, it cannot separate or purify fairly similar compounds such as maltose and dextrose.

EP 452,238 describes a process for making dextrose preparations of above 99% dextrose, which process comprises nanofiltration of a 95–96% DX syrup at about 60° C. This temperature is suggested employed in order to minimize microbial growth problems, to lower viscosity of the retentate thus lowering pumping costs, or to improve mass transfer. Also, EP 452,238 suggests returning the bleed material (which constitutes part of the retentate) to some appropriate upstream point. EP 452,238 is silent with respect to redistribution of the enzyme.

SUMMARY OF THE INVENTION

It has now been found that in a method of producing mono and/or oligosaccharides from starch, including dextrose, trehalose, isomaltooligosaccharides, cyclodextrins and maltooligosaccharides, the efficiency can be improved significantly, and the costs lowered, if in the saccharification (or hydrolyzing) step, after the liquefaction step, the syrup is subjected to one or more high temperature membrane separation steps, and the saccharification enzyme is returned to the saccharification step. According to the method of the present invention, the membrane separation step may be regarded as an integral part of the saccharification step.

In the context of the invention the terms "saccharification step" and "hydrolyzing step" or "saccharifying" and "hydrolyzing" refer to the step after the liquefaction step. The terms are used interchangeably below.

It has also been found that the efficiency of a nanofiltration step, when producing dextrose, can be further increased if the purification process is carried out at an elevated temperature (i.e., of above 63° C.). Moreover, it has been found that the amount of by-products formed during reaction is decreased when a glucose solution (syrup) of a lower glucose content is applied to the membrane separation step. This allow for a more efficient purification of the dextrose syrup, and dextrose preparations, of high purity can be more easily obtained. Finally, yields are improved and costs reduced by employing thermostable enzymes.

When producing saccharides with more than one saccharide unit, i.e., trehalose, isomaltooligosaccharides, cyclodextrins and maltooligosaccharides the hydrolyzing step (after the liquefaction step) is followed by an ultra and microfiltration step or a micro and ultrafiltration step.

Accordingly, in its first aspect, the invention provides a method of saccharifying a liquefied starch solution, which method comprises (i) a saccharification step during which step one or more enzymatic saccharification stages takes place, and the subsequent steps of (ii) one or more high temperature membrane separation steps; and (iii) re-circulation of the saccharification enzyme;

in which method the membrane separation steps are carried out as an integral part of the saccharification step.

In its second aspect, the invention provides a method for the production of a mono and/or oligosaccharide preparation of, e.g., dextrose, trehalose, isomaltooligosaccharides, cyclodextrins and maltooligosaccharides, which method comprises an enzymatic saccharification step, and the subsequent steps of (i) one or more high temperature membrane separation steps; and (ii) re-circulation of the saccharification enzyme.

In a preferred embodiment of producing dextrose the high temperature membrane steps include a micro and ultrafiltration step or a micro and ultrafiltration step in combination with a nanofiltration step.

BRIEF DESCRIPTION OF THE DRAWINGS

The present invention is further illustrated by reference to he accompanying drawing, in which.

DETAILED DISCLOSURE OF THE INVENTION

The Saccharification Method

In its first aspect, the invention provides a method of saccharifying a liquefied starch solution.

In order to obtain an efficient saccharification step, the step -usually comprises one or more stages,. during which the dextrose content of reaction mixture is gradually increased. The saccharification step according to the present invention therefore comprises one or more saccharification stages (Stage 1 to Stage n), as illustrated on figures of the accompanying drawing.

The method comprises the following steps:

(i) a saccharification step during which step one or more enzymatic saccharification stages takes place, and the subsequent steps of (ii) one or more high temperature membrane separation steps; and (iii) re-circulation of the saccharification enzyme.

According to the present invention, the membrane separation step is considered an integral part of the saccharification step, and the membrane separation step may be considered an additional stage of the saccharification step.

In the context of the present invention a high temperature membrane separation step is a membrane separation step accomplished at a temperature of above 60° C., preferably at a temperature of above 63° C., most preferred at a temperature in the range of from about 63 to about 80° C.

In a membrane separation step of the invention, the feed stream subjected to membrane separation originates from the saccharification step, and the retentate from the membrane separation is re-circulated to the saccharification step.

Figure 1:
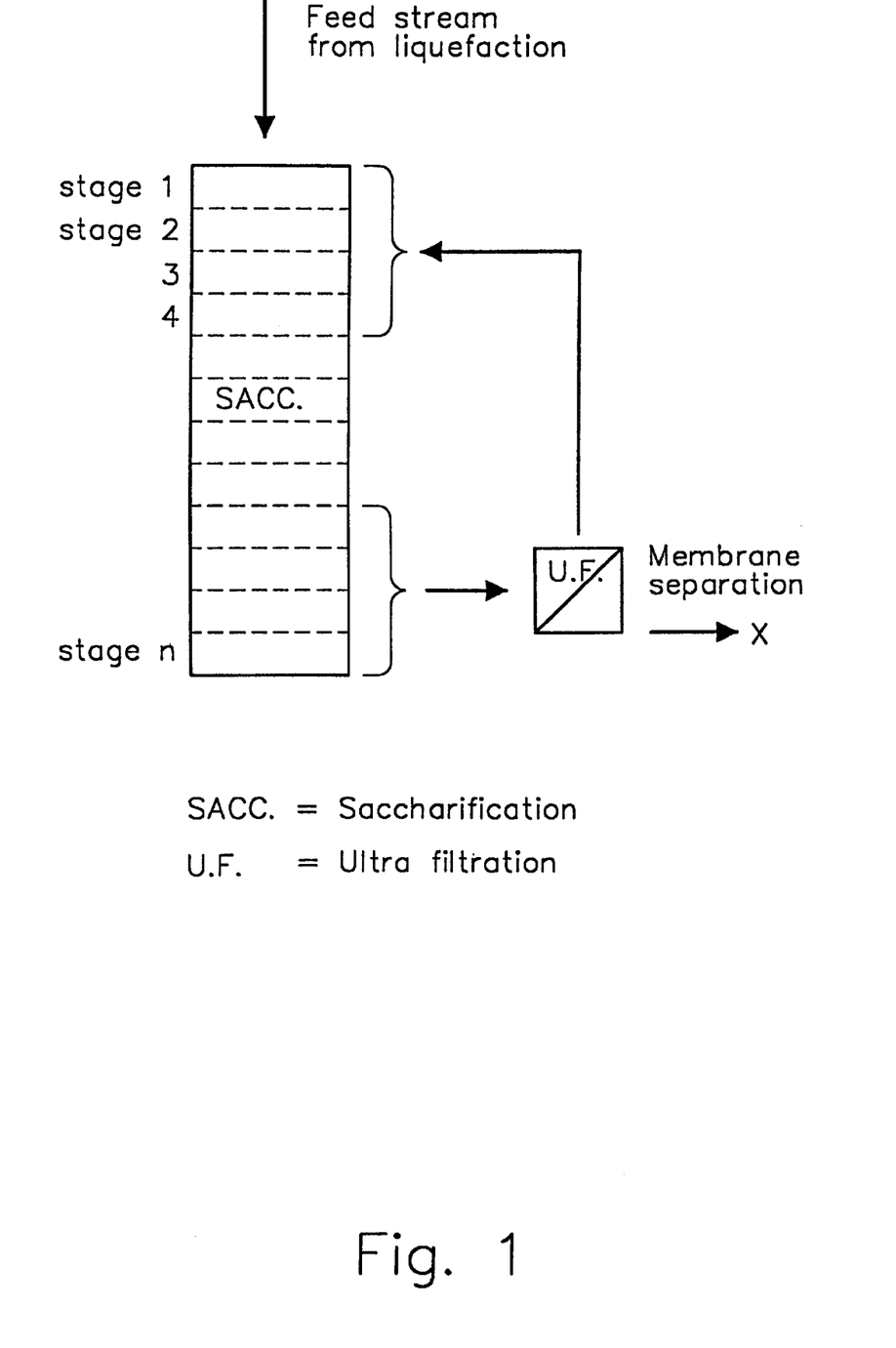
FIG. 1 shows the saccharification step of the invention (SACC), comprising the saccharification stages 1–n, and a membrane separation step of the invention.
Figure 2:
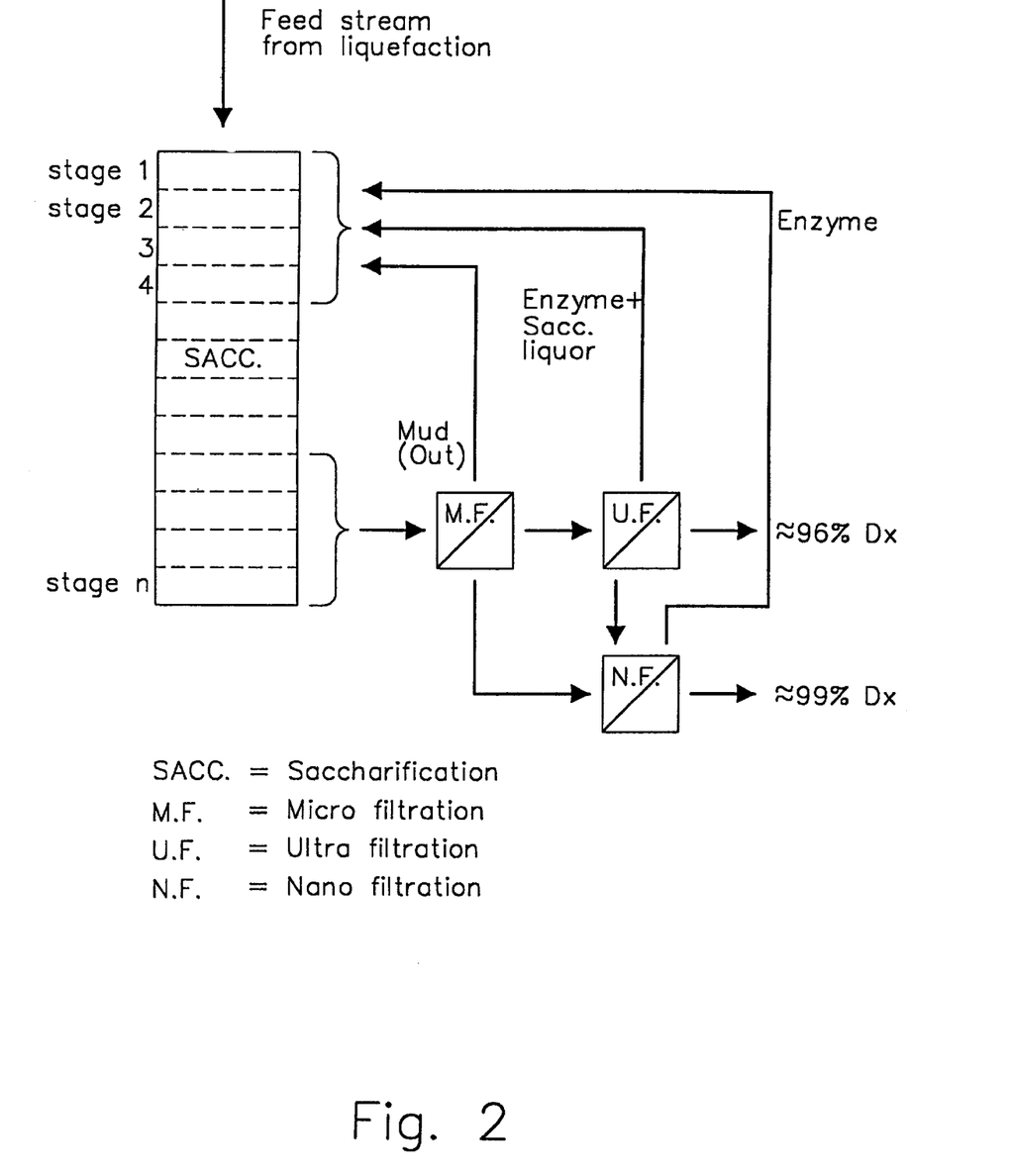
FIG. 2 shows a preferred embodiment of the invention comprising a saccharification step (SACC; including the saccharification stages 1–n), a microfiltration step (MF), an ultrafiltration step (UF), and a nanofiltration step (NF)
Figure 3:
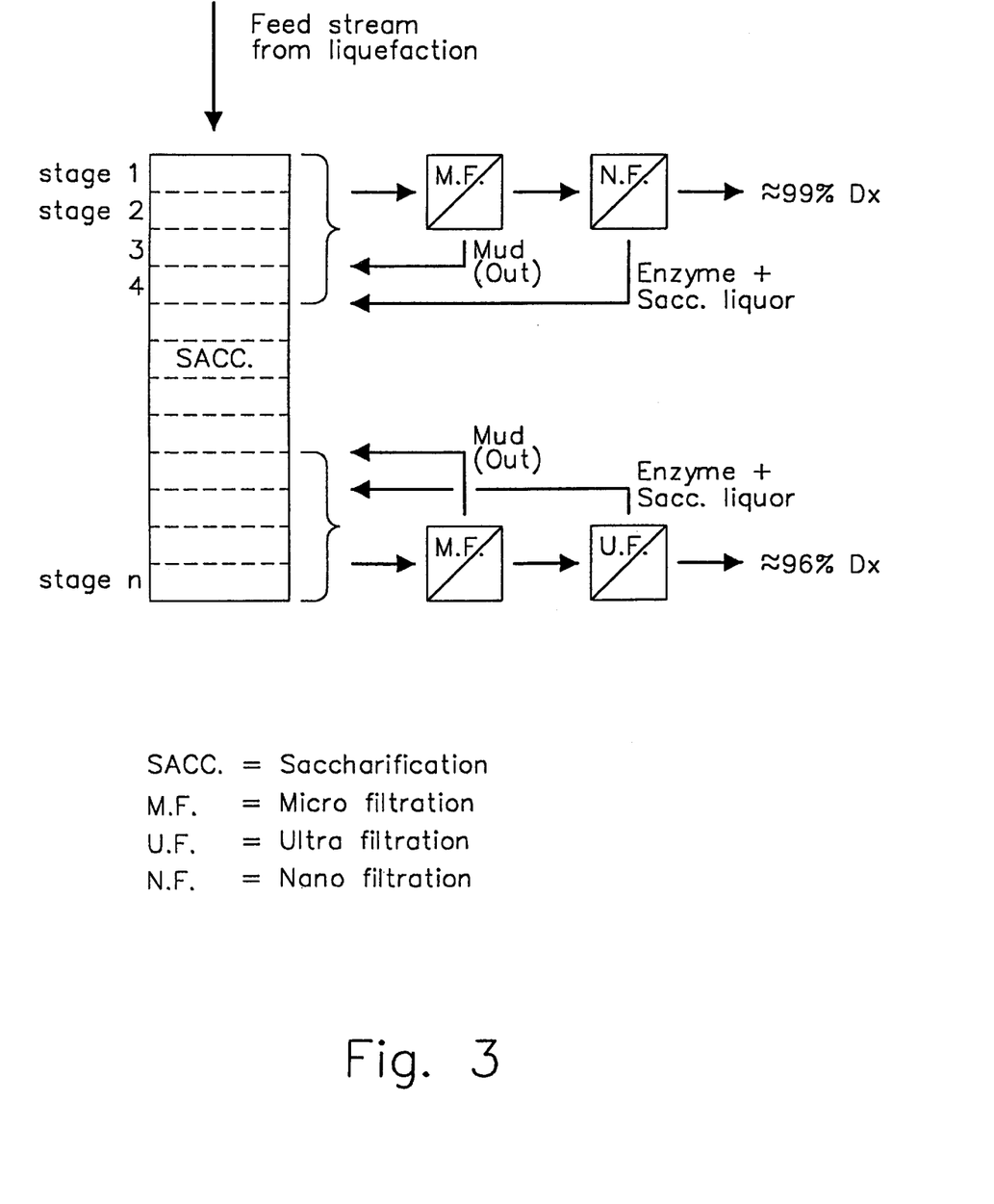
FIG. 3 shows another preferred embodiment of the invention comprising a saccharification step (SACC; including the saccharification stages 1–n), a microfiltration step (MF), an ultrafiltration step (UF), and a nanofiltration step (NF).

As described above, the saccharification step usually comprises one or more saccharification stages (cf. FIG. 1). However, the saccharification step may also be accomplished as one or more batch processes, comprising of from one to a few steps. In a preferred embodiment of the present invention, the saccharification step comprises from 1 to 64 saccharification stages, more preferred from 1 to 32 saccharification stages.

According to the method of the invention, the retentate from the membrane separation is conveyed back (re-circulated) to the saccharification step. Preferably the retentate from the membrane separation is re-circulated to a saccharification stage in the saccharification step, at which stage the content of the reaction mixture matches the content of the retentate with respect to the saccharide, such as glucose, trehalose, isomaltooligosaccharide, cyclodextrin or maltooligosaccharide.

In particular a retentate of, e.g., a high glucose content should not be re-circulated to a saccharification stage in which the glucose content is significantly lower. The same applies to the other saccharides contemplated according to the invention.

In a preferred embodiment, when producing dextrose, the feed stream subjected to membrane separation originating from the saccharification stage holds of from about 50 to about 96% DX, preferably of from about 60 to 96% DX, more preferred of from about 80–96% DX.

When producing maltooligosaccharides, the feed stream subjected to membrane separation originating from the saccharification stage holds of from about 30 to above 80%, such as from 30 to 40% maltose or 50–55% maltose or 55–65% maltose or 70–75% maltose or above 80% maltose.

When producing isomaltooligosaccharides, the feed stream subjected to membrane separation originating from the saccharification stage holds from about 10–40% isomaltose.

When producing trehalose, the feed stream subjected to membrane separation originating from the saccharification stage holds of from about 50 to about 90%, preferably of from about 60 to 90%, more preferred of from about 75–90% trehalose.

When producing cyclodextrins, the feed stream subjected to membrane separation originating from the cyclization step holds of from about 30–60% cyclodextrins.

In the context of the present invention a membrane separation step comprises a microfiltration step, an ultrafiltration step, and/or a nanofiltration step when producing dextrose, i.e., a microfiltration step, an ultrafiltration step, and a nanofiltration step alone or in combination.

In the context of the present invention a membrane separation step comprises a microfiltration step followed by an ultrafiltration step or an ultrafiltration step followed by a microfiltration step when producing trehalose, isomaltooligosaccharides, cyclodextrins and maltooligosaccharides.

A nanofiltration step is not included in the latter case as saccharides larger than glucose cannot flow freely through the nanofiltration membrane.

In Table 1, below, cut-off values characteristic for the various membrane separation processes are stated.

TABLE 1

| Typical Membrane Cut-off Values | |
|---|---|
| Type of Membrane Separation | Cut-off Values (Molecular Weight) |
| Microfiltration | 100,000 to 1,000,000 |
| Ultrafiltration | 2,000 to 100,000 |
| Nanofiltration | 300 to 1,000 |
| Reverse Osmosis | Less than 100 |

In a preferred embodiment, the membrane separation steps comprises a microfiltration step and an ultrafiltration step, applied in the order specified. This embodiment is particularly useful for the production of a syrup holding from about 95 to about 96% glucose, or from 10–40% isomaltose, or 30 to above 80% maltose, or 75–90% trehalose, or 30–60% cyclodextrins.

In a more preferred embodiment, when producing dextrose, the feed stream subjected to membrane separation holds of from about 90 to about 96% DX, in which case the feed stream subjected to membrane separation originates from the late part of the saccharification step, preferably from the very last saccharification stage.

In another preferred embodiment, when producing dextrose, the membrane separation steps comprises a microfiltration step and a nanofiltration step, preferably applied in the order specified. This embodiment is particularly useful for obtaining dextrose preparations of high purity, because of the amount of by-products formed during reaction is decreased when a dextrose solution (syrup) of a lower dextrose content is applied to the membrane separation step. Preferably, the feed stream subjected to membrane separation originating from the saccharification stage should hold of from about 80 to about 92% DX dextrose. This embodiment is ideal for the production of a dextrose preparation holding more than 99% DX, i.e., of from about 99 to 99.8% DX, dextrose. Preferably the feed stream subjected to the membrane separation steps originates from a stage in the middle part of the saccharification step. In a more specific aspect, the retentate is re-distributed to the saccharification step at a saccharification stage located later compared to the stage from which the feed stream originated.

In yet another preferred embodiment, the membrane separation steps comprises a microfiltration step, an ultrafiltration step and a nanofiltration step, preferably applied in the order specified. This embodiment is particularly useful for the production of a dextrose preparation holding of from about 99 to 99.9% DX.

A Method of Manufacturing

In its second aspect, the invention provides a method for the production of a syrup, which syrup is produced by enzymatic conversion of starch in two steps. Enzymatic conversion of starch into sugars involves the subsequent steps of liquefaction and saccharification.

Production of Dextrose

In the saccharification step, a feed stream originating from the liquefaction step is subjected to the action of a glucoamylase enzyme (EC 3.2.1.3), and/or a de-branching enzyme, which may be a pullulanase (EC 3.2.1.41), and/or an isoamylase (EC 3.2.1.68).

Maltooligosaccharide Production

A number of maltooligosaccharide syrups are today being produced in large scale. The below methods are examples of methods for producing typically commercially available product with a high maltose content.

Production of Low Maltose Syrup (Containing 30–40% Maltose)

To produce Low Maltose Syrup starch is liquefied to a DE of 10–20. The temperature and pH of the liquefied starch is adjusted to 70° C. and pH about 5.0, respectively, and is subjected to maltogenic amylase activity (e.g., Maltogenase™ 4000 L, 150 ml/t DS) and α-amylase activity (e.g., Termamyl™ 120 L, 200 g/t DS) for 18–42 hours. The process time depends on the desired saccharide spectrum to be achieved.

The dose of α-amylase activity (e.g., Termamyl™) influence the level of dextrose and maltotriose, i.e., a higher dosage results in higher level. Further, the dose of the maltogenic amylase activity influence the composition so that a higher dosage results in higher dextrose and maltose levels, but a lower maltotriose level.

Production of High Maltose Syrup (Containing 50–55% Maltose)

To produce a High Maltose Syrup starch is liquefied to DE 10–20. The pH and temperature of the liquefied starch is adjusted to 65° C. and to a pH around 5.0, respectively, and is subjected to maltogenic amylase activity (e.g., Maltogenase™ 4000 L, 0.4 l/t DS), pullulanase activity (e.g., Promozyme™ 600 L, 0.3 l/t DS) and a-amylase activity (e.g., BAN 240 L or Termamyl™ 120 L, type LS, 0.4 kg/t DS) for 24–41 hours. The specific process time depends on the desired saccharide spectrum to be achieved. By increasing the dosage of the maltogenic amylase and pullulanase the maltose content can be increased.

Alternatively a High Maltose Syrup may be produced by first liquefying starch to DE 10–20 and then adjusting the pH and temperature to 55° C. and a pH around 5.5, respectively, and subjecting the liquefied starch to a fungal α-amylase activity (e.g., Fungamyl™ 800L) for 22–44 hours. The dosage of fungal α-amylase depends on the saccharification time foreseen, e.g., 200 g/t DS for 44 hours and 400 g/t DS for 22 hours.

To produce a High Maltose Syrup starch with maltose content of 55–65% starch is liquefied to DE 10–20. The pH and temperature of the liquefied starch is adjusted to 60° C. and to a pH around 6, respectively, and is subjected to maltogenic amylase activity (e.g., Maltogenase™ 4000 L, 0.25–1.0 l/t DS), and fungal α-amylase activity (e.g., Fungamyl™ 800 L, 0.4–1.0 kg/t DS) for 24–48 hours.

Alternatively, the liquefied starch may adjusted to a temperature of 65° C. and a pH around 5.0 and subjected to maltogenic amylase activity (e.g., Maltogenase™ 4000 L, 0.5–1.0 l/t DS), and pullulanase activity (e.g., Promozyme™ 600 L, 0.5–1.0 l/t DS) for 18–42 hours.

Production of Very High Maltose Syrup (containing from 70–75% maltose)

To produce a Very High Maltose Syrup starch is liquefied to a DE of max. 10, DS=30%. The pH and temperature of the liquefied starch is adjusted to about 58° C. and a pH around 5.5, respectively, and is subjected to the action of pullulanase activity (e.g., Promozyme™ 600 L, 1 l/t DS), malt extract (approx. 400° Lintner), 3–4 kg/t DS or β-amylase (1500° Lintner), 1 kg/t DS, for about 2 days.

The DE after liquefaction influence the final maltose content, the higher the DE the lower the maltose percentage. The DS influence the final maltose content, the higher the DS the lower the maltose percentage.

Production of Ultra High Maltose Syrup (Containing above 80% Maltose)

To produce a Ultra High Maltose Syrup starch is liquefied to a DE of max. 10, DS=30%. The pH and temperature of the liquefied starch is adjusted 58° C. and a pH around 5.5, respectively, and is subjected to a maltogenic amylase activity (e.g., Maltogenease™, 4000 L, 1.5 l/t DS), pullulanase activity (e.g., Promozyme™ 600 L, 1 l/t DS) and malt extract (1500° Lintner) 1 kg/t DS, for a period of time from 24–72 hours. The specific process time depends on the desired saccharide spectrum to be achieved.

Production of Trehalose (Containing 75–90% Trehalose)

In the saccharification step, when producing trehalose, liquefied starch is subjected to the action of an enzyme capable of first converting maltooligosaccharide (from the liquefaction step) into the non reducing saccharide maltooligosyl trehalose by intramolecular transglycosylation followed by a subsequent step of hydrolyzing the reaction product of the first step (i.e., maltooligosyl trehalose) into trehalose. The saccharification step may be performed using maltooligosyl trehalose synthase (MTSase) and maltooligosyl trehalose trehalohydrolase (MTHase), e.g., the two enzymes described by Masaru et al. (1996), Biosci. Biotech. Biochem., 60 (3), 546–550). MTSase and MTHase act on amylose or starch to produce trehalose.

Another enzymatic process for producing trehalose from starch or maltooligosaccharides (see Kato et al., (1996), Biosci. Biotech. Biochem., 60 (3), p. 546–550) involves using trehalose-producing enzymes, a glycosyltransferase and an amylase, respectively, from the hyperthermophilic archae *Sulfolobus solfataricus* KM1.

Further, EP 764720 also describes using two enzymes from Solfolobus spp. for preparing trehalose from starch or maltooligosacchairdes.

Production of Cyclodextrins (Containing 30–60% Cyclodextrins)

Cyclodextrin Syrups can be produced enzymatically using starch as the starting material. Large scale processing of starch requires jet cooking temperatures of 105–110° C. to liquefy the starch in the first step. After the liquefaction step a CGTase is added to perform a cyclization reaction.

In the case of using a CGTase from a thermophilic anaerobic genus, such as Thermoanaerobacter, a 15–30% DS starch is jet cooked for about 5 minutes at about 105° C., pH 5.0–6.0. The CGTase (25–50 NU/g DS) may be added directly to the jet cooker together with the α-amylase (e.g., Termamyl™). The CGTase will remain active and stable over the temperatures necessary in this step. The following cyclization step is then carried out at temperatures around 90° C. for 4–24 hours.

Production of Isomaltooligosaccharide (Comprising 10–40% Isomaltose)

Isomaltooligosaccharide syryps or "Alo mixtures" may be produced from starch by first performing a liquefaction step using a thermostable bacterial α-amylase. The degree of hydrolysis (DE) of the starch is kept between 6–10. The liquefied starch is then subjected simultaneously to a β-amylase (e.g., soybean β-amylase) and a transglucosidase (e.g., from *Aspergillus niger*), 2–4 g and 0.2–0.3 g/kg starch, respectively, at 60° C., pH 5.0, for about 72 hours. The reaction mixture is purified and concentrated to obtain the isomaltooligosaccharide product.

In order to obtain an efficient saccharification, the saccharification step usually comprises one or more stages, during which the dextrose content of reaction mixture is gradually increased. The saccharification step according to the present invention therefore comprises one or more saccharification stages, as illustrated in the figures of the accompanying drawing.

The method of the invention comprises an enzymatic saccharification step, and the subsequent steps of (i) one or more high temperature membrane separation steps; and (ii) re-circulation of the saccharification enzyme.

In the context of the present invention, a high temperature membrane separation step is a membrane separation step accomplished at a temperature of above 60° C., preferably at a temperature of above 63° C., most preferred at a temperature in the range of from about 63 to about 80° C.

According to the present invention, the membrane separation step may be considered an integral part of the saccharification step. In fact the membrane separation step may also be considered an additional stage of the saccharification step, as described above.

In a membrane separation step of the invention, the feed stream subjected to membrane separation originates from the saccharification step, and the retentate from the membrane separation is re-circulated to the saccharification step.

As described above, the saccharification step usually comprises one or more saccharification stages. In particular the saccharification step may be accomplished as one or more batch processes, comprising of from one to a few steps. In a preferred embodiment of the present invention, the saccharification step comprises of from 1 to 64 saccharification stages, more preferred of from 1 to 32 saccharification stages.

In another preferred embodiment, the feed stream subjected to membrane separation originates from a saccharification stage in the last half part of the stages constituting the saccharification step. Preferably the feed stream subjected to membrane separation originates from the very last saccharification stage.

According to the method of the invention, the retentate from the membrane separation is conveyed back (re-circulated) to the saccharification step. More specifically the retentate from the membrane separation is re-circulated to a stage in the saccharification step at which stage the content of the reaction mixture match the content of the retentate with respect to glucose (as determined by DX). In particular a retentate of a high glucose content should not be re-circulated to a saccharification stage in which the glucose content is significantly lower.

In a preferred embodiment, when producing dextrose, the feed stream subjected to membrane separation originating from the saccharification stage holds of from about 50 to about 90%, preferably of from about 60 to 90%, more preferred of from about 75–90% glucose.

When producing maltooligosaccharide syrups, the feed stream subjected to membrane separation originating from the saccharification stage holds of from about 30 to above 80%, such as from 30 to 40% maltose or 50–55% maltose or 55–65% maltose or 70–75% maltose or above 80% maltose.

When producing isomaltooligosaccharide syrups, the feed stream subjected to membrane separation originating from the saccharification stage holds from about 10–40% isomaltose.

When producing trehalose, the feed stream subjected to membrane separation originating from the saccharification stage holds of from about 50 to about 90%, preferably of from about 60 to 90%, more preferred of from about 75–90% trehalose.

When producing cyclodextrins, the feed stream subjected to membrane separation originating from the cyclization step holds of from about 30–60% cyclodextrins.

In the context of the present invention, when producing dextrose, a membrane separation step comprises a microfiltration step, an ultrafiltration step, and/or a nanofiltration step. In Table 1, above, cut-off values characteristic for the various membrane separation processes are stated.

In a preferred embodiment, the membrane separation steps comprises a microfiltration step and an ultrafiltration step, applied in the order specified. This embodiment is particularly useful for the production of a dextrose preparation holding of from about 95 to about 96% DX. In a more preferred embodiment, the feed stream subjected to membrane separation holds of from about 90 to about 96% DX, in which case the feed stream subjected to membrane separation originates from the late part of the saccharification step, preferably from the very last saccharification stage.

In another preferred embodiment, the membrane separation steps comprises a microfiltration step and a nanofiltration step, applied in the order specified. This embodiment is particularly useful for obtaining dextrose preparations of high purity, because of the amount of by-products formed during reaction is decreased when a dextrose solution (syrup) of a lower dextrose content is applied to the membrane separation step. Preferably, the feed stream subjected to membrane separation originating from the saccharification stage should hold of from about 80 to about 92% DX dextrose. This embodiment is ideal for the production of a dextrose preparation holding more than 99% DX, i.e., of from about 99 to 99.8% DX, dextrose. Preferably the feed stream subjected to the membrane separation steps originates from a stage in the middle part of the saccharification step. In a more specific aspect, the retentate is re-distributed to the saccharification step at a saccharification stage located later compared to the stage from which the feed stream originated.

In yet another preferred embodiment, the membrane separation steps comprises a microfiltration step, an ultrafiltration step and a nanofiltration step, preferably applied in the order specified. This embodiment is particularly useful for the production of a dextrose preparation holding of from about 99 to 99.9% DX.

Thermostable Glucoamylase Enzymes

Preferably, the saccharification step of the invention is performed in presence of a thermostable glucoamylase enzyme (EC. 3.2.1.3).

Saccharification including using a thermostable AMG may be carried out as described in Example 3.

In a preferred embodiment the glucoamylase enzyme has a half-life ($T_{1/2}$) at 70° C. of above 5–10 hours, determined in the presence of 30% maltodextrin.

In another preferred embodiment the glucoamylase used for the saccharification method of the invention has a residual activity higher that the wild-type *A. niger* AMG (SEQ ID NO: 2), determined as described in the Materials and Methods section, i.e., determined as residual activity after incubation for 30 minutes in 50 mM NaOAc, pH 4.5, 70° C., 0.2 AGU/ml.

The glucoamylase enzyme may preferably be derived from a strain of Aspergillus, in particular *Aspergillus niger* or *Aspergillus luchuenesis*, a strain of *Trichoderma viride*, a strain of Rhizopus sp., in particular a strain of *Rhizopus niveus*, a strain of Endomyces sp., a strain of *Cephalosporium cherticola*, a strain of Clostridium, in particular *Clostridium thermoamylolyticum*, *Clostridium thermosulphurogenes* and *Clostridium thermohydrosulphuricum*, a strain of Pestalotiopsis, or a strain of Talaromyces, in particular *Talaromyces duponti, Talaromyces emersonii* and *Talaromyces thermophilus*.

In a preferred embodiment the glucoamylase is a fungal glucoamylase derived from a strain of *Aspergillus niger* with a substitution in one or more of the following positions (using the SEQ ID NO: 2 numbering): S119P, N20C, A27C, S30P, G137A. In a further preferred embodiment the *A. niger* glucoamylase (AMG) has the following substitution (s): N20C+A27C+S30P+G137A; N20C+A27C; S30P; N20C+A27C+S30P; G137A; S30P+G137A.

Thermostable De-branching Enzymes

Preferably, the saccharification step of the invention is performed in presence of a thermostable de-branching enzyme. Preferably, the de-branching enzyme is a pullulanase (EC 3.2.1.41) or an isoamylase (EC 3.2.1.68).

A thermostable pullulanase may be derived from a strain of Bacillus, in particular *Bacillus naganoenis* or *Bacillus acidopullulyticus*, a strain of Clostridium, in particular *Clostridium thermosulphurogenes* and *Clostridium thermohydrosulphuricum*, or a strain of Pyrococcus, in particular *Pyrococcus woesie* and *Pyrococcus furiosus*.

A thermostable isoamylase may be derived from a strain of Flavobacterium, in particular *Flavobacterium odoratum*, a strain derived from the thermophilic acrhaebacterium *Sulfolobus acidocaldarius* (Hayashibara, (1996) Biochimica et Biophysica Acta 1291, p. 177–181, such as *Sulfolobus acidocaldarius* ATCC33909 and from a strain of *Rhodethermus marius*.

Fungal α-amylase

In an embodiment, the saccharification step of the invention is performed in presence of a thermostable α-amylase, preferably a fungal α-amylase.

A fungal α-amylase may be derived from a strain of Aspergillus, in particular *Aspergillus niger* or *Aspergillus oryzae*, or a strain of Acremonium.

The invention is further illustrated with reference to the following examples which are not intended to be in any way limiting to the scope of the invention as claimed.

Bacterial α-amylases

When using a bacterial α-amylase in the saccharification step of the invention it may suitable be performed in presence of a thermostable bacterial α-amylase, such as a Bacillus α-amylase, such as the commercially available *B. licheniformis* (e.g., Termamyl™ from Novo Nordisk) or variants thereof. Another suitable thermostable amylase is the maltogenic amylase from *Bacillus stearothermophilus* (e.g., Maltogenase™ from Novo Nordisk).

Beta-amylase

In an embodiment, the saccharification step of the invention is performed in presence of a β-amylase. β-amylase are often derived from plants such as soybeans and barley.

Transglucosidase

When using a transglucosidase in the saccharification step aa *Aspergillus niger* transglucosidase may be used (available from, e.g., Amano).

MTSase and MTHase

Preferably, the saccharification step, when producing trehalose is performed in presence of a MTSase and MTHase, e.g., the enzymes disclosed by Masaru et al. (1996), Biosci. Biotech. Biochem., 60 (3), 546–550).

Thermostable CGTases

When producing cyclodextrins the cyclization step may preferably be performed in the presence of a thermostable CGTase. Suitable thermostable CGTases include the CGTases from the thermophilic anaerobic genus Thermoanaerobacter, the genus Bacillus, such as *B. macerans, B. circulans, B.sterothermophilus*, and *B. subtilis*.

MATERIAL AND METHODS

Enzymes

Dextrozyme®: A balanced mixture of glucoamylase and pullulanase obtained from selected strains of *Aspergillus niger* and *Bacillus acidopullulyticus*, respectively, available from Novo Nordisk.

AMG G2: Truncated *Aspergillus niger* glucoamylase G1 is shown in SEQ ID NO: 2, available from Novo Nordisk). *Aspergillus niger* glucoamylase G1 is disclosed in Boel et al., (1984), EMBO J. 3 (5), 1097–1102, available from Novo Nordisk.

Host Cell

*A. oryzae* JaL 125: *Aspergillus oryzae* IFO 4177 available from Institute for Fermention, Osaka; 17–25 Juso Hammachi 2-Chome Yodogawa-ku, Osaka, Japan, having the alkaline protease gene named "alp" (described by Murakami K et al., (1991), Agric. Biol. Chem. 55, p. 2807–2811) deleted by a one step gene replacement method (described by G. May in "Applied Molecular Genetics of Filamentous Fungi" (1992), p. 1–25. Eds. J. R. Kinghorn and G. Turner; Blackie Academic and Professional), using the *A. oryzae* pyrG gene as marker. Strain JaL 125 is further disclosed in WO 97/35956 (Novo Nordisk).

Equipment

MF unit (micro-filtration unit) with a Koch membrane.

NF unit (nano-filtration unit) with a Desal membrane

Koch microfiltration membrane (Koch 3838-MFK-618-FYT) from KOCH Membrane Systems, Inc.

Desal nano-filtration membrane (Desal DL 3840 C1103) from DESAL Membrane Products.

Figure 5:
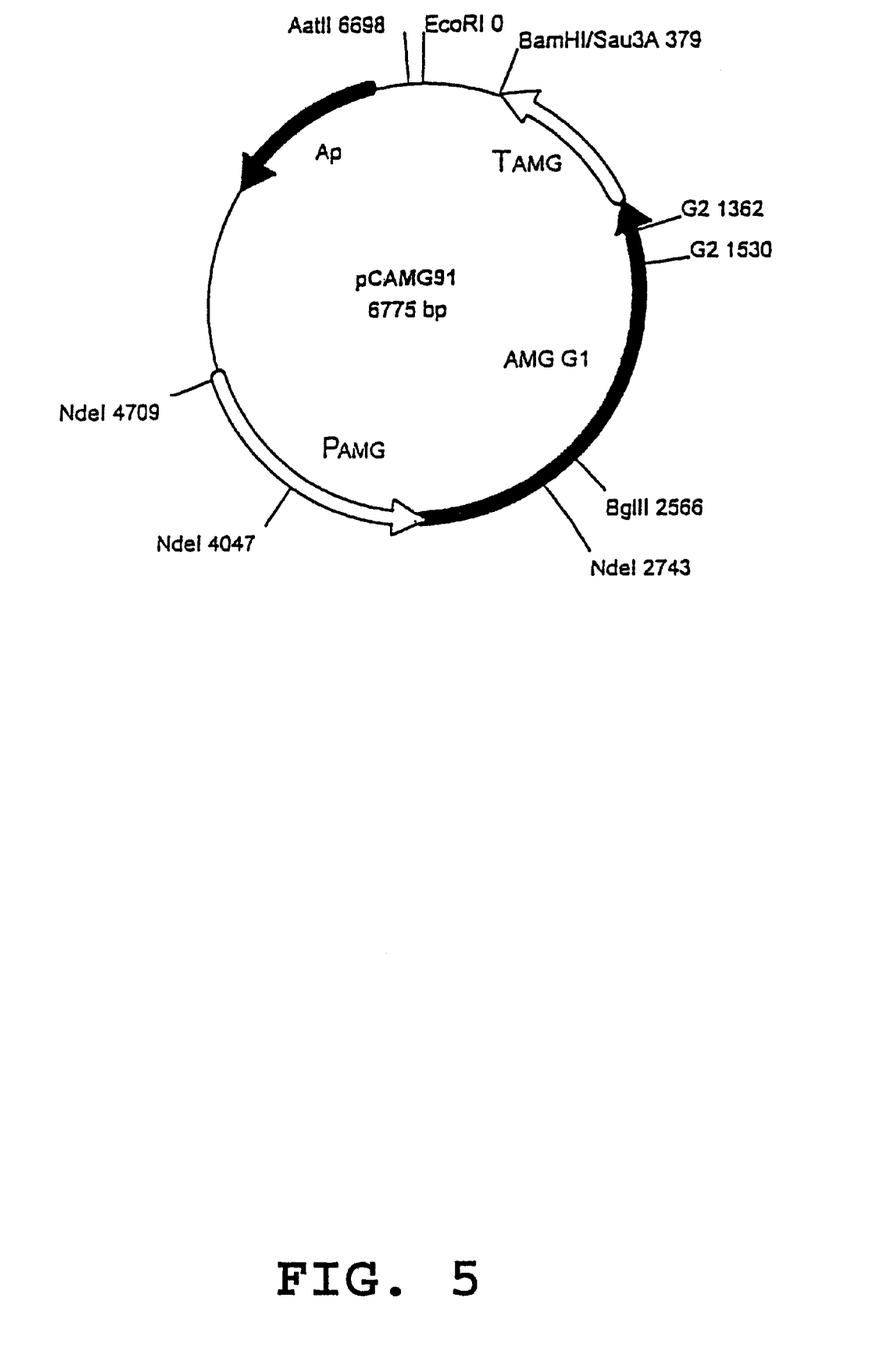
FIG. 5 shows the plasmid pCAMG91 containing the *Aspergillus niger* G1 glucoamylase gene.

Plasmids pCAMG91: see FIG. 5. Plasmid comprising the *Aspergillus niger* G1 glucoamylase (AMG G1). The construction of pCAMG91 is described in Boel et al., (1984), EMBO J. 3 (7) p.1581–1585.

pMT838: Plasmid encoding the truncated *Aspergillus niger* glucoamylase G2 (SEQ ID NO: 2).

Methods

Activity Definitions for Dextrozyme™

One AGU (Novo Amyloglucosidase Unit) is the amount of enzyme which under specific conditions hydrolyzes one micromole of maltose per minute.

One PUN (pullulanase Unit Novo) is the amount of enzyme which under specified conditions hydrolyzes pullulan, liberating reducing carbohydrate with a reducing power equivalent to one micromole of glucose per minute.

Detailed descriptions of the analytic methods are available on request from Novo Nordisk.

Determination of AGU Activity

One Novo Amyloglucosidase Unit (AGU) is defined as the amount of enzyme which hydrolyzes 1 micromole maltose per minute under the following standard conditions:

Substrate . . . maltose

Temperature . . . 25° C.

pH . . . 4.3 (acetate buffer)

Reaction time . . . 30 minutes

A detailed description of the analytical method (AF22) is available on request.

Transformation of *Aspergillus oryzae* (General Procedure)

100 ml of YPD (Sherman et al., (1981), Methods in Yeast Genetics, Cold Spring Harbor Laboratory) are inoculated with spores of *A. oryzae* and incubated with shaking for about 24 hours. The mycelium is harvested by filtration through miracloth and washed with 200 ml of 0.6 M $MgSO_4$. The mycelium is suspended in 15 ml of 1.2 M $MgSO_4$, 10 mM $NaH_2PO_4$, pH 5.8. The suspension is cooled on ice and 1 ml of buffer containing 120 mg of Novozym™ 234 is added. After 5 min., 1 ml of 12 mg/ml BSA (Sigma type H25) is added and incubation with gentle agitation continued for 1.5–2 hours at 37° C. until a large number of protoplasts is visible in a sample inspected under the microscope.

The suspension is filtered through miracloth, the filtrate transferred to a sterile tube and overlayed with 5 ml of 0.6 M sorbitol, 100 mM Tris-HCl, pH 7.0. Centrifugation is performed for 15 min. at 1000 g and the protoplasts are collected from the top of the $MgSO_4$ cushion. 2 volumes of STC (1.2 M sorbitol, 10 mM Tris-HCl, pH 7.5, 10 mM $CaCl_2$) are added to the protoplast suspension and the mixture is centrifugated for 5 min. at 1000 g. The protoplast pellet is resuspended in 3 ml of STC and re-pelleted. This is repeated. Finally, the protoplasts are resuspended in 0.2–1 ml of STC.

100 μl of protoplast suspension are mixed with 5–25 μg of p3SR2 (an *A. nidulans* amdS gene carrying plasmid described in Hynes et al., Mol. and Cel. Biol., Vol. 3, No. 8, 1430–1439, Aug. 1983) in 10 μl of STC. The mixture is left at room temperature for 25 min. 0.2 ml of 60% PEG 4000 (BDH 29576), 10 mM $CaCl_2$ and 10 mM Tris-HCl, pH 7.5 is added and carefully mixed (twice) and finally 0.85 ml of the same solution are added and carefully mixed. The mixture is left at room temperature for 25 min., spun at 2.500 g for 15 min. and the pellet is resuspended in 2 ml of 1.2M sorbitol. After one more sedimentation the protoplasts are spread on minimal plates (Cove, (1966), Biochem. Biophys. Acta 113, 51–56) containing 1.0 M sucrose, pH 7.0, 10 mM acetamide as nitrogen source and 20 mM CsCl to inhibit background growth. After incubation for 4–7 days at 37C spores are picked, suspended in sterile water and spread for single colonies. This procedure is repeated and spores of a single colony after the second re-isolation are stored as a defined transformant.

Fed Batch Fermentation

Fed batch fermentation is performed in a medium comprising maltodextrin as a carbon source, urea as a nitrogen source and yeast extract. The fed batch fermentation is performed by inoculating a shake flask culture of *A. oryzae* host cells in question into a medium comprising 3.5% of the carbon source and 0.5% of the nitrogen source. After 24 hours of cultivation at pH 5.0 and 34° C. the continuous supply of additional carbon and nitrogen sources are initiated. The carbon source is kept as the limiting factor and it is secured that oxygen is present in excess. The fed batch cultivation is continued for 4 days, after which the enzymes can be recovered by centrifugation, ultrafiltration, clear filtration and germ filtration. Further purification may be done by anion-exchange chromatographic methods known in the art.

Purification

The culture broth is filtrated and concentrated using Filtron™ ultrafiltration module with 10 kD membranes. The concentrated solution is diafiltrated with 20 mM sodium acetate(EKV-buffer), pH 5 to the conductivity in the concentrate is below 2 mS/cm.

The concentrate is applied on a Pharmacia S Sepharose column FF previously equilibrated in EKV-buffer, pH 5. The column is washed with EKV-buffer, and the amylase is collected in the effluent.

The effluent is added active coal to a concentration of 0.5% and incubated at room temperature for 10 minutes. The coal is then removed by filtration.

Finally, the enzyme solution is subjected to a Pharmacia Q Sepharose FF column previously equilibrated in EKV-buffer, pH 4.3. The column is washed with EKV-buffer, and bound proteins are eluted with a linear NaCl gradient from 0–500 mM NaCl over 10 column volumes. Glucoamylase containing fractions are pooled.

Homogeneity of the purified product is analyzed by SDS-PAGE. The gel is stained with Coomassie Blue.

Thermal Stability Determination of Glucoamylase (AMG)

The thermal stability of a glucoamylase is tested using the following method: 950 microliter 50 mM sodium acetate buffer (pH 4.3) (NaOAc) is incubated for 5 minutes at 70° C. 50 microliter enzyme in buffer (4 AGU/ml) is added. 2×40 microliter samples are taken at 0 and 30 minutes and chilled on ice. The activity (AGU/ml) measured before incubation (0 minutes) is used as reference (100%). The decline in percent is calculated as a function of the incubation time.

$T_{1/2}$ (Half-life) of a Glucoamylase

The $T_{1/2}$ is measured by incubating the glucoamylase (0.18–0.36 AG/g DS) in question in 30% 10 DE maltodextrin at pH 4.5 at the temperature in question (e.g., 70° C.). Samples are withdrawn at set time intervals and further incubated at 50° C. for 24 hours to ensure that all substrate is hydrolysed, since maltodextrin might affect the activity assay. Incubation at 50° C. for 24 hours will not reduce the enzyme activity significantly. After incubation the samples are cooled and residual enzyme activity measured by the pNPG method (as described below).

The % residual glucoamylase activity is determined at different times. $T_{1/2}$ is the period of time until which the % relative activity is decreased to 50%.

Residual Enzyme Activity (pNPG Method)

pNPG Reagent 0.2 g pNPG (p-nitrophenylglucopyranoside) is dissolved in 0.1 M acetate buffer (pH 4.3) and made up to 100 ml.

Borate Solution 3.8 g $Na_2B_4O_7.10\ H_2O$ is dissolved in Milli-Q water and made up to 100 ml.

AMG Standard

An aqueous enzyme solution containing a known amount of enzyme equivalent to 0.04 AGU/ml.

Samples might be diluted prior to analysis (1:1–1:2 with water). The following solutions are prepared:

HS: 0.5 ml sample+1 ml AMG standard+3 ml pNPG reagent

H: 0.5 ml sample+1 ml water+3 ml pNPG reagent

B: 0.5 ml sample+1 ml AMG standard+3 ml borate solution

Place HS and H in a 50° C. water bath. After 2 hours, 3 ml borate solution is added to each vial. B is placed at room temperature and 3 ml pNPG reagent added after 2 hours. The optical density of all three solutions are measured at 400 nm, and the activity calculated:

$$\text{Activity} = 2 \ast AGU_{st} \ast (H-B)/(HS-H)$$

where HS, H, and B are the OD of the solutions analyzed, and $AGU_{st}$ is the activity of the AMG standard used.

EXAMPLES

Example 1

Saccharification to Produce Dextrose Liquor

Figure 4:
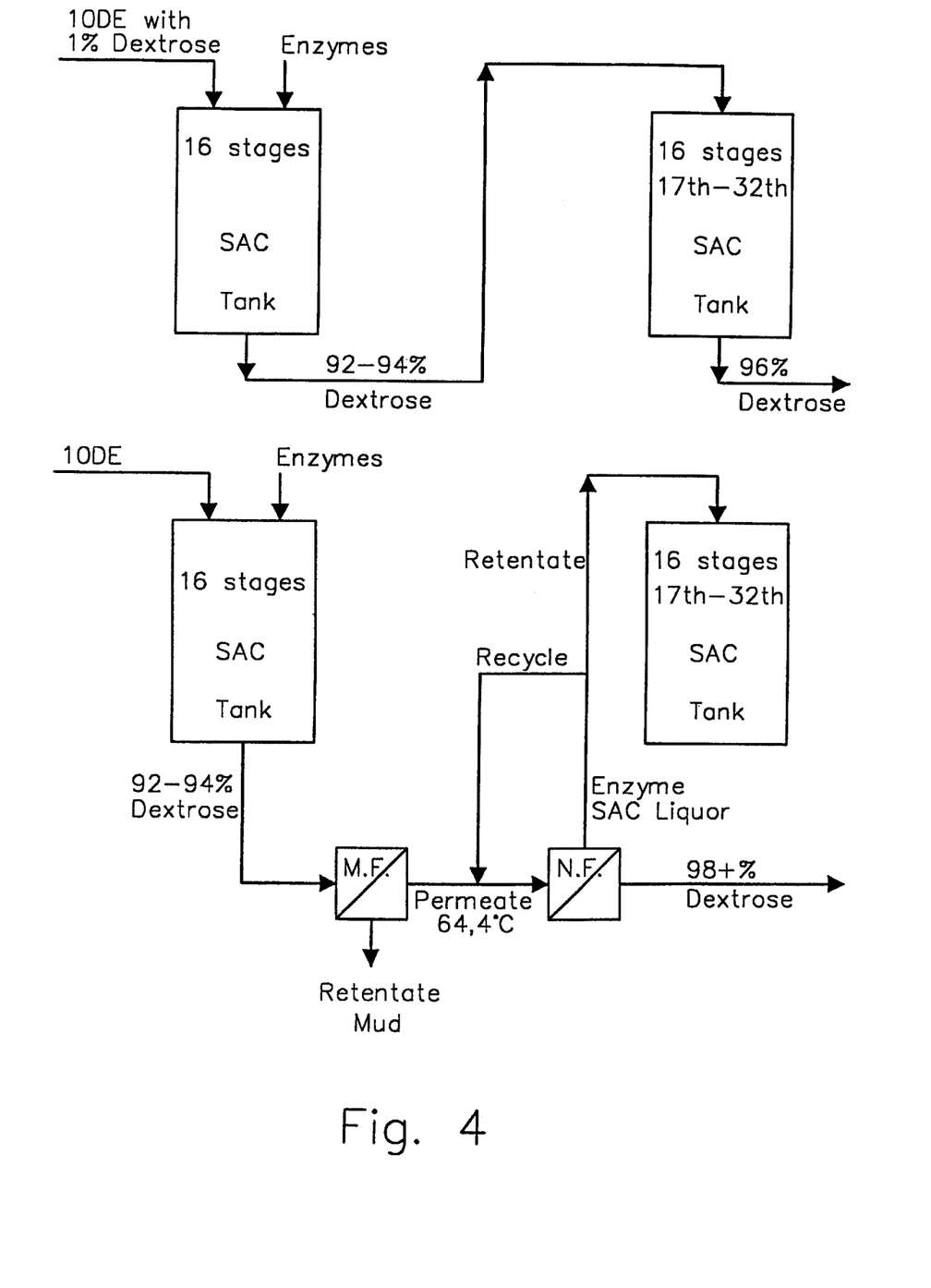
FIG. 4 shows a block diagram of dextrose saccharification process of the invention using two saccharification tanks (SAC Tank) with each 16 stages with an MF unit and a NF unit placed in between the two tanks.

The dextrose saccharification process of the invention was carried out using two 16 stage tanks (a total of 32 stages) (see FIG. 4). A MF unit and a NF unit were placed between the $16^{th}$ and the $17^{th}$ stage of the two saccharification tanks.

The saccharification membrane liquor from the $16^{th}$ stage of the first saccharification tank containing 1) 92–94% dextrose syrup, 2) Dextrozyme™ (0.18 AGU per grams Dry Solids (DS)), and 3) Mud was used as feed to the MF unit.

The retentate of the MF unit is the mud. The permeate of the MF unit is the saccharification liquor and the Dextrozyme®.

The permeate of the MF unit was used as the feed to NF unit. The permeate of the NF unit contains about 99% dextrose, as only the dextrose and water are small enough to pass through the nano membrane. The retentate of the NF unit was sent to the $17^{th}$ stage of the second saccharification tank wherein the saccharification was continued to yield 96% dextrose without adding any more Dextrozyme®. About 28 GPM enzyme was recycled to the permeate feed to the NF unit.

The data recorded during the experiment are:

Vender: Desal

Spacer Thickness: 45 ml

Model#: DL3840 C1103

Area (ft²): 60

Serial#: 6013758

Gal/ft²/Day (GFD) ml/min* 0.006340

| Time Run hours | Pressure in/out PSI | Flow Circ GPM | Temp Feed °C. | Dry Solids Feed % DS | Dry solids Perm % DS | Flow Perm ml/min | Rate Perm GFD | % Dex + Fruc. Feed % Mono | % Dex + Fruc. Perm % Mono |
|---|---|---|---|---|---|---|---|---|---|
| 6 | 600/590 | 28 | 64.4 | 33.6 | 23.8 | 1000 | 6.50 | | |
| 8 | 600/590 | 28 | 64.4 | 34.2 | 24.6 | 980 | 6.10 | | |
| 10 | 600/590 | 28 | 64.4 | 34.2 | 24.5 | 980 | 6.00 | 95.79 | 99.82 |
| 12 | 600/590 | 28 | 64.4 | 34.6 | 24.8 | 880 | 5.60 | | |
| 14 | 600/590 | 28 | 64.4 | 35.4 | 25.2 | 860 | 5.30 | | |
| 16 | 600/590 | 28 | 64.4 | 35.8 | 25.7 | 840 | 5.30 | | |
| 18 | 600/590 | 28 | 64.4 | 35.9 | 25.7 | 840 | 5.30 | | |
| 20 | 600/590 | 28 | 64.4 | 35.8 | 25.7 | 840 | 5.30 | 94.20 | 99.84 |

Remarks: Bleed Out from Retentate Line 1 to 1 with Permeate Flow

Flow Circ.: Recycled enzyme; Temper Feed: Temperature in the feed stream to the NF unit. % Dry solid Feed: % Dry solids in the feed stream introduced into the NF unit; % dry solid Perm; % Dry solids in the permeate from the NF unit; % Mono: % monosaccharides of DS; GPM: Gallons per minute; PSI: pressure; % DS: % Dry solids.

According to the saccharification process of the invention membrane filter units are used as an integral part of the saccharification process.

As can be seen from the Table 1 above the dextrose yield is above 99%.

Example 2

Construction of a Thermostable AMG G2 S119P Variant Site-directed Mutagenesis

For the construction of variants of a AMG G2 enzyme (SEQ ID NO: 2) the commercial kit, Chameleon doublestranded, site-directed mutagenesis kit was used according to the manufacturer's instructions.

The gene encoding the AMG G2 enzyme in question is located on pMT838 prepared by deleting the DNA between G2 nt. 1362 and G2 nt. 1530 in plasmid pCAMG91 (see FIG. 1) comprising the AMG G1 form.

In accordance with the manufacturer's instructions the ScaI site of the Ampicillin gene of pMT838 was changed to a MluI site by use of the following primer:

7258: 5'p gaa tga ctt ggt tga cgc gtc acc agt cac 3'(SEQ ID NO: 3).

(Thus changing the ScaI site found in the ampicillin resistance gene and used for cutting to a MluI site). The pMT838 vector comprising the AMG gene in question was then used as a template for DNA polymerase and oligo 7258 (SEQ ID NO. 3) and 21401 (SEQ ID NO: 4).

Primer no. 21401 (SEQ ID NO: 4) was used as the selection primer.

21401: 5'p gg gga tca tga tag gac tag cca tat taa tga agg gca tat acc acg cct tgg acc tgc gtt ata gcc 3'

(Changes the ScaI site found in the AMG gene without changing the amino acid sequence).

The desired mutation (e.g., the introduction of a cystein residue) is introduced into the AMG gene in question by addition of an appropriate oligos comprising the desired mutation.

The primer SP119P was used to introduce S119P

P-CCTACACTG GTCCTTGGGG ACGGC    (SEQ ID NO: 5)

The mutation are verified by sequencing the whole gene. The plasmid was transformed into *A. oryzae* using the method described above in the "Materials and Methods" section. The variant was fermented and purified as described above in the "Materials and Methods" section.

The residual activity after incubation for 30 minutes in 50 mM NaOAc, pH 4.5, 70° C., 0.2 AGU/ml was determined as listed in the Table below and compared to the wild-type *A. niger* AMG.

| A. niger AMG (Enzyme) | Residual activity (%) |
|---|---|
| S119P variant | 22 |
| wild-type (SEQ ID NO: 2) | 13 |

Example 3

Saccharification Using a Thermostable AMG Variant to Produce Dextrose Liquor

The saccharification described in Example 1 is repeated, except that the AMG of Dextrozyme™ is replaced with the *A. niger* S119P variant of Example 2.

What is claimed is:

1. A method of producing one or more monosaccharides and oligosaccharides, comprising the steps of:
   (a) subjecting a liquefied starch solution to saccharification which comprises more than one enzymatic saccharification stage;
   (b) subjecting the saccharification liquor from one of the saccharification stages to a microfiltration step;
   (c) subjecting the permeate of the microfiltration step to a nanofiltration step;
   (d) re-circulating the retentate from the nanofiltration step to a saccharification stage of step (a), at which saccharification stage the content of the reaction mixture matches the content of the retentate with respect to the mono or oligosaccharide, and
   (e) recovering the permeate of the nanofiltration step which comprises one or more monosaccharides and oligosaccharides.

2. The method of claim 1, wherein the saccharification comprises between 16 and 64 enzymatic saccharification stages.

3. The method according to claim 1, wherein the product from the nanofiltration step is a dextrose preparation with from 99 to 99.9% DX.

4. The method of claim 1, wherein the saccharification step is performed in the presence of a glucoamylase (E.C. 3.2.1.3).

5. The method of claim 4, wherein the method is carried out in the presence of a de-branching enzyme.

6. The method of claim 5, wherein the de-branching enzyme is a pullulanase (EC 3.2.1.41) or an isoamylase (EC 3.2.1.68).

7. The method of claim 4, wherein the method is carried out in the presence of an α-amylase.

8. A method of producing one or more monosaccharides and oligosaccharides, comprising the steps of:
   (a) subjecting a liquefied starch solution to saccharification which comprises more than one enzymatic saccharification stage;
   (b) subjecting the saccharification liquor from one of the saccharification stages to a microfiltration step;
   (c) subjecting the permeate of the microfiltration step (b) to a nanofiltration step;
   (d) recovering the permeate of the nanofiltration step which comprises the one or more monosaccharides and oligosaccharides,
   (e) subjecting the retentate from the nanofiltration step (d) to more than one further saccharification stages,
   (f) subjecting the saccharification liquor from step (e) to a microfiltration step;
   (g) subjecting the permeate obtained from the microfiltration step (f) to an ultrafiltration step;
   (h) re-circulating the retentate from the ultrafiltration step (g) to a saccharification stage, wherein said saccharification stage follows the middle stage in the saccharification step; and
   (j) recovering the permeate of the ultrafiltration which comprises one or more monosaccharides and oligosaccharides.

9. The method of claim 8, wherein the saccharification comprises between 16 and 64 enzymatic saccharification stages.

10. The method of claim 8, wherein the retentate from the nanofiltration step (d) is a dextrose preparation with from 99 to 99.9% DX.

11. The method according to claim 8, wherein the product recovered from the ultrafiltration step (j) is a dextrose preparation with from 80 to 96% DX.

12. The method of claim 8, wherein the saccharification step is performed in the presence of a glucoamylase (E.C. 3.2.1.3).

13. The method of claim 12, wherein the method is carried out in the presence of a de-branching enzyme.

14. The method of claim 13, wherein the de-branching enzyme is a pullulanase (EC 3.2.1.41) or an isoamylase (EC 3.2.1.68).

15. The method of claim 13, wherein the method is carried out in the presence of an α-amylase.

* * * * *